United States Patent [19]

Belonenko et al.

[11] Patent Number: 5,836,200
[45] Date of Patent: Nov. 17, 1998

[54] CELL FOR MEASURING ACOUSTICAL PROPERTIES OF FLUID SAMPLES UNDER HIGH PRESSURE

[75] Inventors: Vladimir Belonenko; Eugenij Bünau, both of Moscow, Russian Federation; Tigran Chalikian, Piscataway, N.J.; Theodor Funck, Göttingen, Germany; Vijcheslav Nikolashev, Moscow; Armen Sarvazyan, Pushchino, both of Russian Federation

[73] Assignee: UHP Corp., Portola Valley, Calif.

[21] Appl. No.: 586,925

[22] PCT Filed: Aug. 9, 1993

[86] PCT No.: PCT/EP93/02113

§ 371 Date: Aug. 7, 1996

§ 102(e) Date: Aug. 7, 1996

[87] PCT Pub. No.: WO95/04929

PCT Pub. Date: Feb. 16, 1995

[51] Int. Cl.$^6$ .............................. G01N 29/02; G01H 5/00
[52] U.S. Cl. ...................... 73/61.79; 23/64.53; 23/24.06; 23/597
[58] Field of Search ............................ 73/579, 597, 32 A, 73/19.03, 19.1, 24.06, 30.04, 31.05, 54.41, 61.49, 61.79, 64.53, 645, 702, 703, 721, 862.59, 594, 571, 38, 856, 73, 794; 310/324, 328

[56] References Cited

U.S. PATENT DOCUMENTS

| | | | |
|---|---|---|---|
| 2,521,634 | 3/1950 | Janssen et al. | 73/24.01 |
| 3,807,222 | 4/1974 | Eggers | 73/24.01 |
| 4,377,087 | 3/1983 | Rodot | 73/594 |
| 4,380,930 | 4/1983 | Podhrasky et al. | 73/594 |
| 4,961,345 | 10/1990 | Tsuruoka et al. | 73/32 A |
| 5,060,506 | 10/1991 | Douglas | 73/24.01 |
| 5,178,005 | 1/1993 | Peterson | 73/597 |
| 5,392,635 | 2/1995 | Cadet et al. | 73/24.01 |
| 5,542,298 | 8/1996 | Sarvazian et al. | 73/597 |

FOREIGN PATENT DOCUMENTS

A0502197  8/1991  European Pat. Off. .

Primary Examiner—Hezron E.. Williams
Assistant Examiner—Rose M. Miller
Attorney, Agent, or Firm—Baker & Botts, L.L.P.

[57] ABSTRACT

A cell for measuring acoustical properties for fluid sample includes a stack consisting essentially of a first end piece (20), a first, wafer-shaped electro-acoustical transducer (18), a main body (12), a second electro-acoustical transducer (16) and a second end piece (22). C-shaped clamps (24) or other means are used to apply pressure on the stack. The main body (12) and the end pieces (20, 22) form axially extending, aligned cavities (14, 29, 31). The main body (12) and each end piece (20, 22) has a radial channel (28; 32) which extends from the respective cavity to an opening at a circumferential surface. A thin elastic membrane (50) tightly encloses the stack. An annular member (51) is forced in each channel opening urging a portion of the sleeve (50) into the respective channel to form a pressure resistant seal.

16 Claims, 16 Drawing Sheets

CELL FOR MEASURING ACOUSTICAL PROPERTIES OF FLUID SAMPLES UNDER HIGH PRESSURE

FIELD OF THE INVENTION

The present invention relates to measurement of acoustical properties of fluid samples, more specifically to cells for performing such measurement.

BACKGROUND OF THE INVENTION

Acoustical methods for determining acoustical parameters of fluid samples, such as speed and attenuation of acoustical waves, and cells for performing such measurements are well known in the art. A preferred method for investigating fluid samples of small volume is the so-called resonator method.

A measurement cell for use in a resonator method is disclosed in international patent application, publication No. WO 92/03732, inventors Sarvazyan, Belonenko and Chalikian. This cell comprises a pair of thin, flat, waver-like electro-acoustical transducers which are positioned on opposite front faces of an essentially cylindrical cell body to define at least one resonator chamber adapted to receive a liquid sample to be investigated. A plurality of sample chambers which share the same pair of electro-acoustical transducer wafers may be provided in a single cell body to provide comparison measurements of test samples and fluids of known properties.

The cell disclosed in the Sarvazyan, Belonenko and Chalikian application is a sandwich structure or stack comprising an essential cylindrical main body forming the sample chamber or chambers, an acoustic transducer on each side of the main body and closing the axial ends of the sample chamber(s), and means for holding this structure together, i.e. end pieces and axial bolts or annular screw caps. Each sample chamber is accessible by a radial aperture in the wall of the main body through which a sample can be introduced. This aperture is closed by a flexible tubular membrane member which surrounds the cell body and serves to separate the sample from the surrounding. In operation the measurement cell is placed in an autoclave containing a pressurizing liquid. The pressure of the pressurizing liquid is increased by means of a piston pump and transmitted to the sample liquid by the flexible member which separates the sample and pressurizing liquids. One of the transducers is energized by high-frequency electrical waves of varying frequency and an output signal is obtained from the other transducer and processed to obtain desired information.

As A. P. Sarvazyan et al. disclose in Ultrasonics 29 (1991) pp. 119–124 each transducer of an acoustical resonator cell can be backed with liquid. In high pressure work the stress imposed on the transducers by a pressurized sample can be reduced by backing the transducers with the pressurizing liquid.

The known cells for acoustical measurements suffer from several drawbacks. First, the structure of the known cells is complicated and expensive to manufacture. The delicate, thin and brittle transducers must be carefully mounted and provided with apertures for accommodating axial bolts which hold the structure together. The bolts must be tightened with utmost care to avoid subjecting the delicate, thin and brittle transducers to excessive and uneven stresses.

A second problem is the compensation of the pressure exerted by the pressurized sample fluid on the transducers. Even if liquid backing is used, the known cells cannot be used for sample pressures exceeding about 20 MPa (200 bar).

It has been found that the cause of this problem is the flexible member which is used in the known cells to separate the sample fluid from the surrounding pressure transmitting fluid. The flexible membrane of the known cells must be relatively strong to secure proper sealing. When this strong membrane is deformed to pressurize the sample the deformation force unbalances the pressures of the fluids adjacent the front and back surfaces of the transducers which impairs the performances of the transducers. Eventually this may cause rupture of the transducers.

The flexible elastic membrane member used for sealing the sample chambers is also the cause of another problem. Under high pressure, capillary forces tend to cause the fluid into which the cell is submerged for pressurizing to creep into the sample chamber from the outside of the cell along the interface between the membrane and the surface of the cell body so that the sample fluid is spoiled. This problem cannot be solved by using stronger membranes because this will increase the pressure unbalance across the transducers explained above. Reliable separation of the pressurizing fluid and the sample fluid is therefore not possible at high pressures, which in practice may exceed 100 MPa (1000 bar).

Still another problem encountered with the known cells is the difficulty to fill the sample chamber completely with sample fluid. Completely filling the sample chamber with fluid is necessary because any entrapped air or gas will prevent the generation of high pressure in the sample fluid and deteriorate the measurements because of the high compressibility of gases in comparison with that of liquids. A common procedure to fill the sample chamber of an acoustic measurement cell is to evacuate the sample chamber then introduce the sample fluid. This is not only cumbersome but may also change the composition of the sample fluid by selective evaporation of components of the sample fluid.

SUMMARY OF THE INVENTION

It is an objective of the invention to provide a cell for determining acoustical parameters of a sample fluid which is simple and easy to manufacture.

A further objective of the invention is to provide a cell for acoustical measurements under high pressure which provides reliable separation of the sample fluid from the pressurizing fluid.

Another objective of the invention is to provide a cell for acoustical measurements which avoids excessive and/or non-uniform stresses of the transducers and impairement of the performance of the transducers by pressure differences.

Still another objective of the invention is to provide a cell which can be easily completely filled with a sample fluid. These problems are solved by a cell for measuring acoustical properties of a fluid sample, said cell comprising:

a main cell having
(a) a cell body having first and second flat cell ends opposite each other,
(b) first and second cell openings in the first and second flat cell ends, respectively,
(c) a fluid sample cavity in the cell body for receiving the fluid sample, the fluid sample cavity being in communication with the first and second cell openings, and
(d) a fluid sample channel connecting the fluid sample cavity and the outer surface of the cell body;

first and second electro-acoustical transducer wafers disposed on the first and second flat cell ends, respectively, each of the first and second electro-acoustical transducer wafers having an inner surface facing inwardly toward the fluid sample cavity and an outer surface facing outwardly away from the fluid sample cavity;

first and second inner electrodes disposed on the inner surfaces of the first and second electro-acoustical transducer wafers, respectively;

first and second outer electrodes disposed on the outer surfaces of the first and second electro-acoustical transducer wafers, respectively;

a first end piece having (a) a first end-piece body with two ends, (b) a first end-piece end-wall at one end of the end-piece body, (c) a first flat end-piece face at the other end of the end-piece body, the first flat end-piece face being placed in contact with the outer surface of the first electro-acoustical transducer wafer, (d) a first end-piece opening in the first flat end-piece face, the first end-piece opening being approximately the size of and being aligned with the first cell opening, (e) a first compensation fluid cavity for receiving a compensation fluid, the first compensation fluid cavity being in communication with the first end-piece opening, and (f) a first compensation fluid channel connecting the first compensation fluid cavity and the outer surface of the first end-piece body;

a second end piece having (a) a second end-piece body with two ends, (b) a second end-piece end-wall at one end of the end-piece body, (c) a second flat end-piece face at the other end of the end-piece body, the second flat end-piece face being placed in contact with the outer surface of the second electro-acoustical transducer wafer, (d) a second end-piece opening in the second flat end-piece face, the second end-piece opening being approximately the size of and being aligned with the second cell opening, (e) a second compensation fluid cavity for receiving a compensation fluid, the second compensation fluid cavity being in communication with the second end-piece opening, and (f) a second compensation fluid channel connecting the second compensation fluid cavity and the outer surface of the second end-piece body;

first and second terminals mounted in the first and second end pieces, respectively, the first and second terminals electrically coupled to the first and second outer electrodes, respectively;

means for applying pressure to the first and second end pieces to bias them towards each other; and one or more elastic sleeves tightly enclosing the cell body and the first and second end-piece bodies.

Preferably, an elastic retaining member, such as one or a plurality of resilient C-shaped clamps or clips or a helical spring are provided to exert axial pressure on the above described stack of cell components to hold it together.

According to another preferred feature of the invention, the adjacent ends of the cell body and each end piece are formed with aligned circumferential grooves to receive an annular member or ring for centering the transducer positioned between said ends. In addition, means, such as axial recesses may be provided in the grooves which in cooperation with corresponding extensions of the centering rings determine the mutual angular position of the cell body and the end pieces.

The construction and assembly of the measurement cells according to the invention is simplified by using clamps, springs and similar fixing elements mounted on the outside of the cell assembly to maintain the stack of cell components in position and bias it by applying axial pressure. These elements provide a well defined and uniform axial pressure on the stack.

A first measure for providing reliable separation of the sample and pressurizing fluids is provided by manufacturing the mating surfaces of the cell stack with extremely high flatness and small roughness so that capillary forces can not cause the pressurizing fluid to penetrate between the mating surfaces even at moderate axial pressure urging said surfaces together.

Secondly, an extremely thin and compliant elastic membrane or sleeve material surrounding said body and end pieces is urged into the radial apertures by clamping rings or plugs to seal the radial apertures of the cell body and end pieces for reliably separating the sample liquid from the pressurizing liquid. The elastic material may be as thin as 0.2 mm and less so that no noticeable pressure difference can develop across the elastic element even at pressures up to and exceeding 150 MPa (1500 bar). Thus, for equalizing the pressures on the opposite sides of the transducers, the apertures of the end pieces are provided with similar elastic membranes as the filling apertures of the sample chamber.

Alternatively or in addition, the parameters of the cell including the configurations of the chamber and cavities may be designed under consideration of any difference of the compressibilities of the sample and pressurizing liquids in accordance with the following formula:

$$2(C/C_0)+C\beta_0 V_0 = C_1\beta_1 V_1$$

wherein $C$=Volume elasticity of the elastic membrane sealing the sample cavity $C_0$=Volume elasticity of the material of the transducers $C_1$=Volume elasticity of the elastic membrane sealing the compensation cavities $\beta_0$=Coefficient of compressibility of the sample fluid $\beta_1$=Coefficient of compressibility of the liquid within the compensation cavities $V_0$=Volume of sample cavity $V_1$=Volume of compensation cavities.

The measures have the effect that the cavities in the end pieces are exposed to the same pressure as the sample chamber thus, avoiding any build-up of a detrimental pressure difference across the transducers and greatly enhancing the precision of the measurements.

BRIEF DESCRIPTION OF THE DRAWINGS

Further objects, advantages and features of the invention will become apparent from the following description of preferred embodiments in connection with the accompanying drawings, in which

FIGS. 18b and FIG. 18c are sectional and plan views, respectively of a component of the cell of FIG. 18a;

DESCRIPTION OF THE PREFERRED EMBODIMENTS

Figure 1:
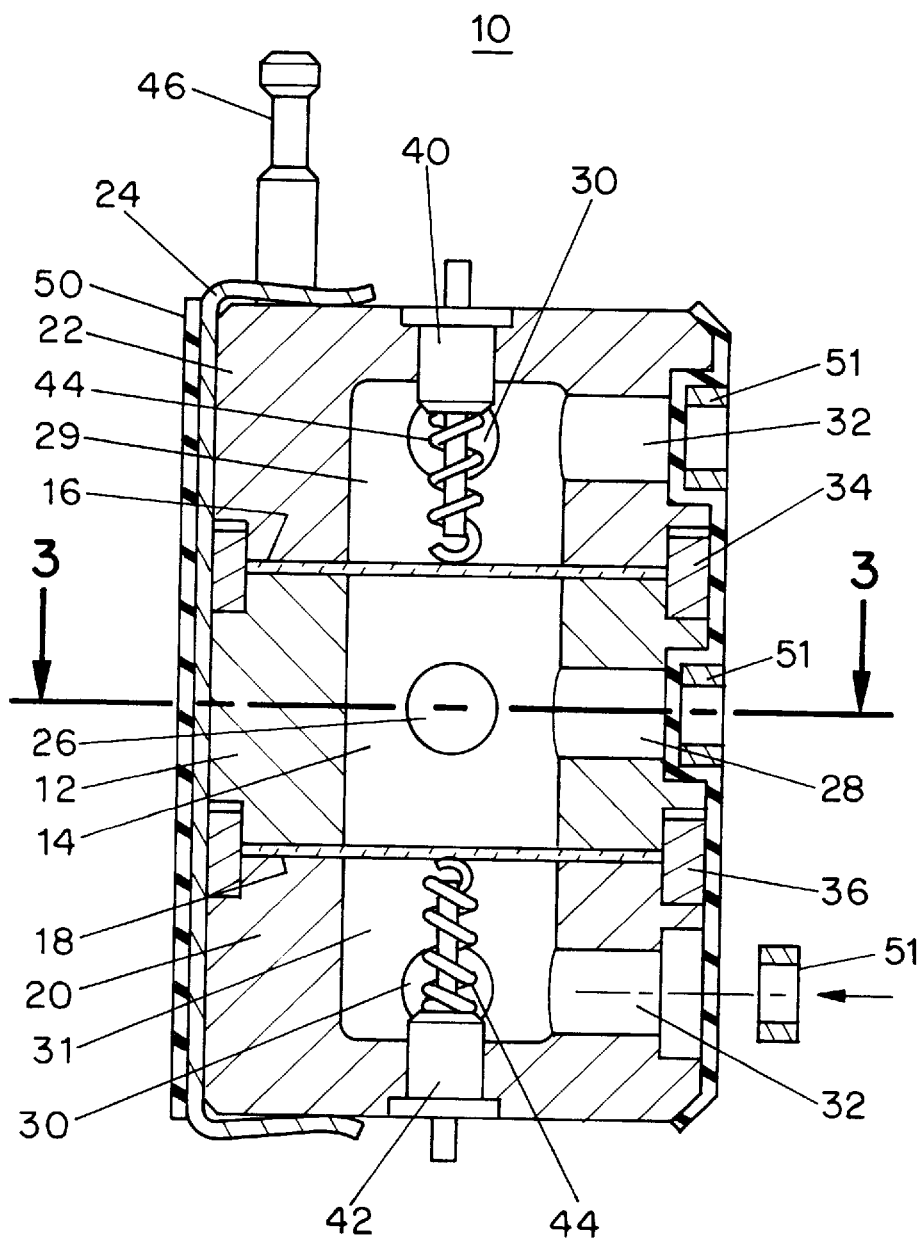
FIG. 1 is a sectional elevation view of an acoustical measurement cell according to a first embodiment of the invention, the section being along a line 1A–A in FIG. 2.
Figure 2:
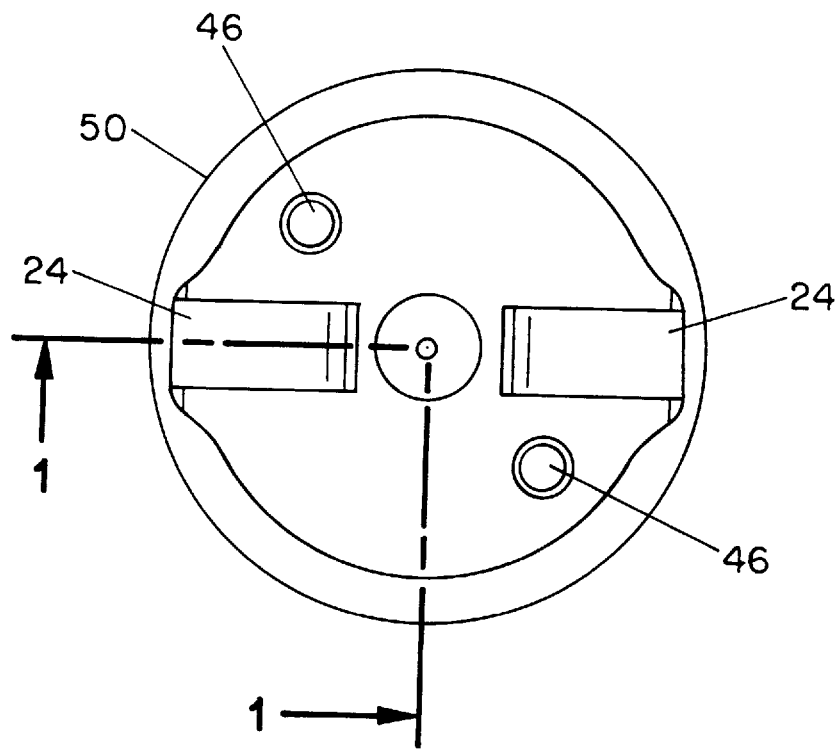
FIG. 2 is a top view of the cell of FIG. 1.
Figure 3:
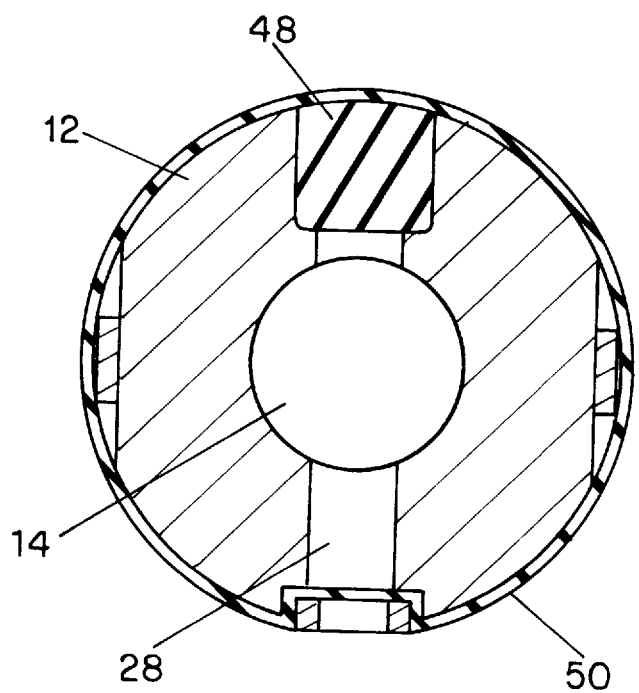
FIG. 3 is a cross-section along a line B—B in FIG. 1.

A preferred embodiment of a measurement cell according to the invention is shown in FIGS. 1 to 3. The cell 10 comprises an essentially cylindrical main body 12 which defines a cylindrical axial resonator cavity 14, further first and second electro-acoustical transducers 16, 18, and end pieces 20, 22 which are stacked as shown in FIG. 1. A pair of essentially C-shaped spring clamps 24 positioned on opposite sides of the stack hold the stack together and exert a well defined axial pressure on the elements of the stack.

The spring clamps 24 are received by axially extending recesses of the outer wall of the main body 12 and the end pieces 20, 22 so that the spring clamps do not increase the radial dimension of the cell assembly.

The main body 12 has two diametrically aligned radial apertures 26, 28 which extend from the resonator cavity 14 to the cylindrical outer wall of body 12. Each end piece 20, 22 forms a compensation cavity 29, 31, respectively which is axially aligned with the sample cavity 14. A pair of radial apertures 30, 32 is provided in each end piece 20, 22. Apertures 26 and 30 have an enlarged outer portion. Apertures 28, 32 have a relatively shallow countersunk outer portion.

The body 12 has opposite end faces which are as flat and smooth as possible, i.e. polished. The same applies to the end face of each end piece which abuts the adjacent transducer. The transducers 16, 18 bear an electrode (not shown) on each main surface. The electrode is formed by a thin layer of gold or any other suitable metal. The flatness and smoothness of the end faces of the body 12 and the end pieces 20, 22 which abut the equally flat main surfaces of the transducers prevent penetration of pressurized fluid from the outside of the cell into the resonator cavity.

In the embodiment shown, the outer cylindrical surfaces of the body 12 and the end pieces 20, 22 form opposed aligned circumferential grooves. Each pair of grooves forms an annular recess serving as seat for an annular member 34, 36, respectively, which serves as centering ring for the adjacent transducer 16, 18, respectively. The annular members 34, 36 also provide for proper axial alignment of the body 12 and the end pieces 20, 22 and facilitate the assembly of the stack.

Each end piece has an axial center hole for accomodating a terminal which comprises an insulating plug 40, 42 with a lead-through conductor and a spring 44 contacting the outside electrode of the respective transducer and serves for electrical connection of this electrode. The terminal forms a pressure-tight seal of the center hole.

The end piece 22 is provided with axially protruding mounting elements 46 which serve for mounting the cell in a pressure vessel or autoclave (not shown).

As shown in FIG. 3, a plug 48 made of rubber or another suitable elastic material is provided in the outer enlarged portion of holes 26, 30. Further, a thin tubular sleeve 50 surrounds the cell assembly and closes the holes 28, 30, 32, of the body 12 and the end pieces 20, 22.

In use, the resonator cavity 14 is filled with a liquid sample by means of a syringe, the hypodermic needle of which is pierced through the plug 48. When the sample fluid is injected, the air is displaced and escapes through the aperture 28 lifting the elastic sleeve 50 slightly. In the same way, preferably before the injection of the sample fluid, the cavities 29, 31 of the end pieces are filled with pressurizing liquid or another suitable liquid.

A clamping ring 51 is forced tightly into the outer countersunk portion of each aperture 28 and 32 after the cavities have been filled with appropriate liquids. The ring 51 urges the elastic sleeve into the respective aperture and forms a seal which resists the occurring pressure differences.

The cell is then mounted in an autoclave (not shown) filled with pressurizing liquid preferably a dielectric liquid such as ethanol, which in turn is pressurized by a piston pump or the like as well known in the art.

Figure 4:
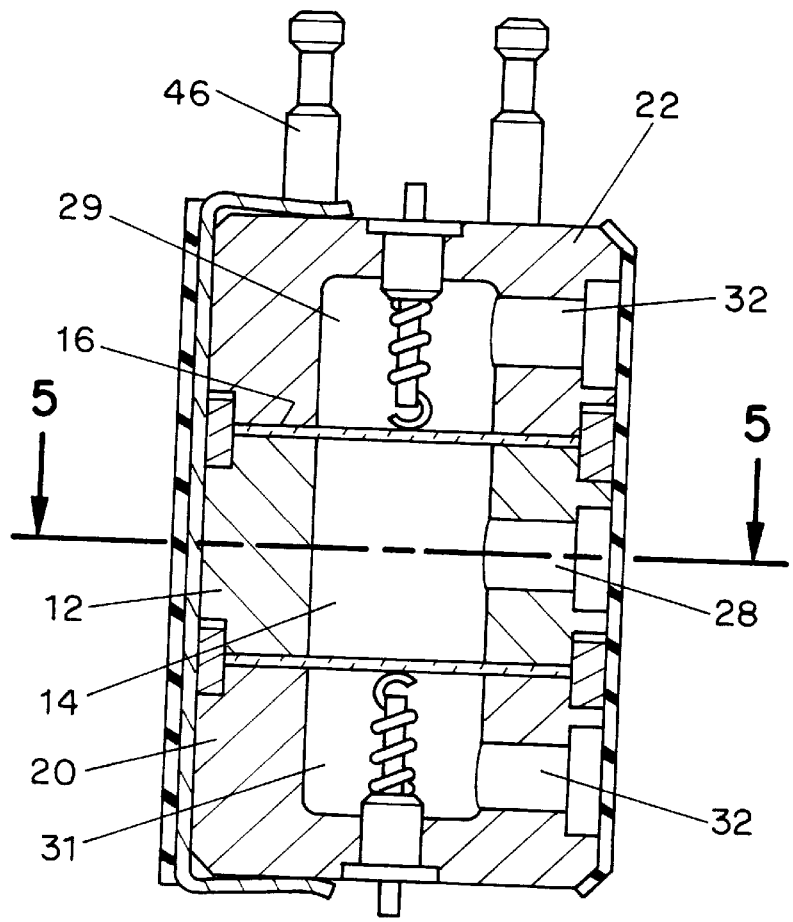
FIG. 4 is a sectional view corresponding to FIG. 1 of another embodiment of the invention.
Figure 5:
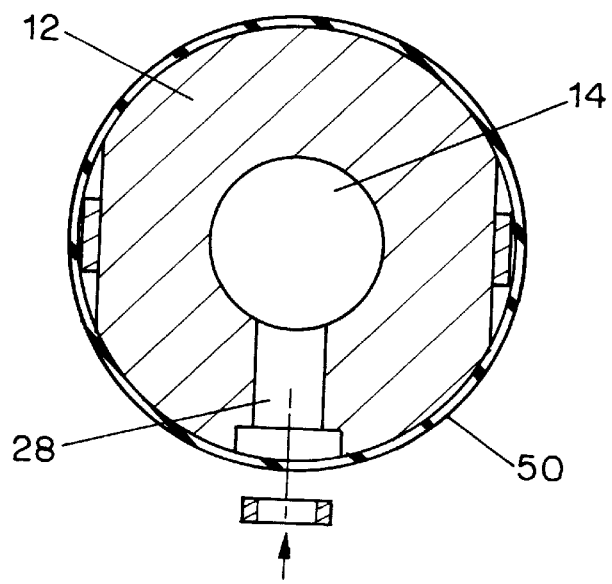
FIG. 5 is a sectional view along a line V—V of FIG. 4.

The cell shown in FIGS. 4 and 5 differs from the cell of FIGS. 1 to 3 in that only one radial aperture 28, 32 is provided in the body 12 and each end piece 20, 22. For filling the cavities 14, 29, and 31, a removable tube is used for filling the cavities 14, 29 and 31 with liquid. A preferred method and apparatus for cavities of this and the following cells will be explained in more detail with reference to FIGS. 19a, 19b and 19c.

Figure 6:
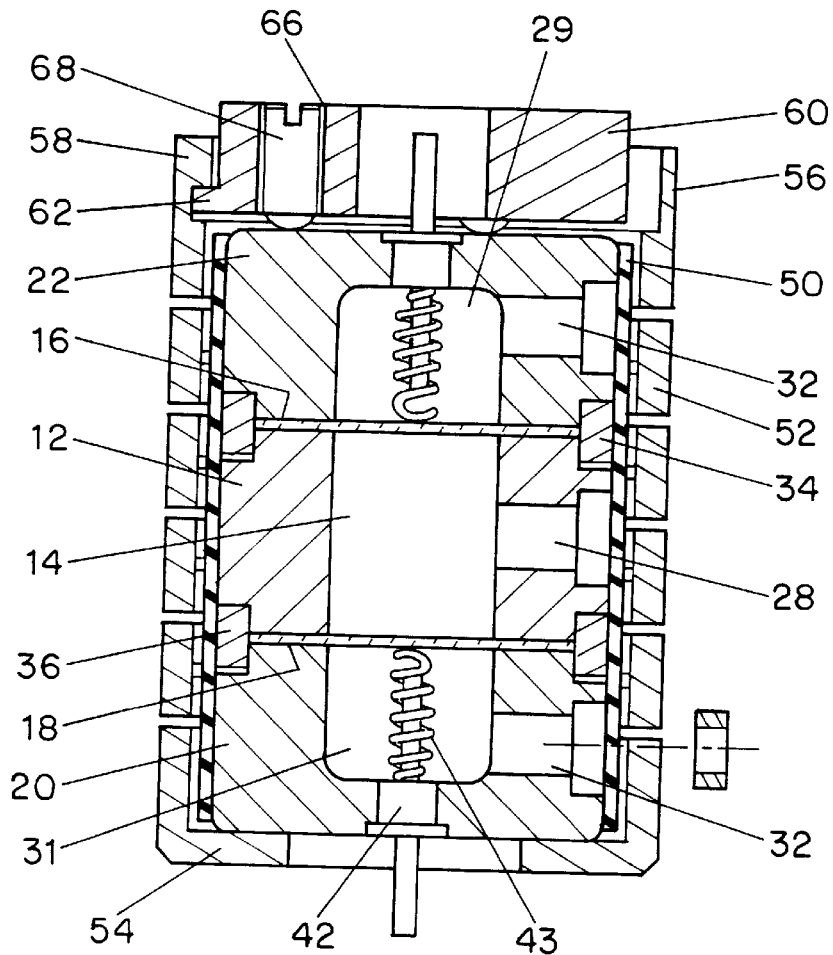
FIG. 6 is a sectional elevation view of a third embodiment of the invention.
Figure 7:
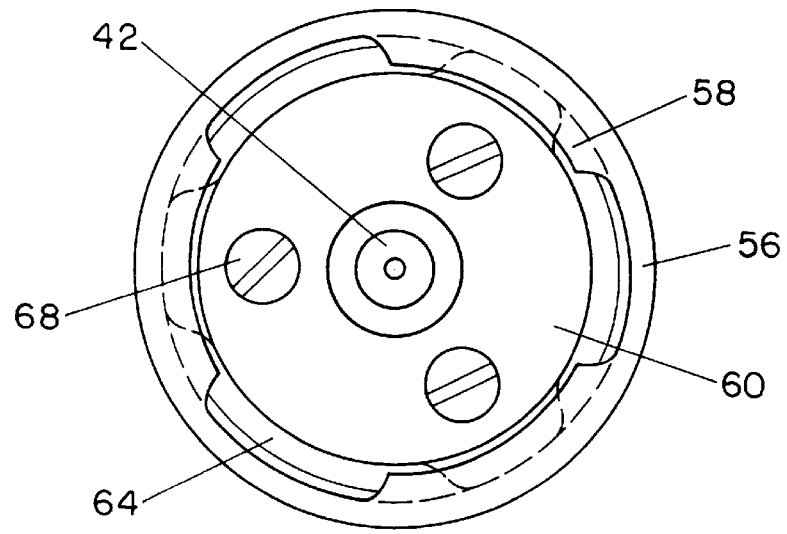
FIG. 7 is a top view of the embodiment of FIG. 6.

FIGS. 6 and 7 show a measurement cell which is similar to that of FIGS. 4 and 5 with the exception that the stack forming the cell proper is axially biased by a resilient element rather than by C-shaped clamps. More specifically, the stack consisting of the end piece 20, the transducer 18, the body 12, the transducer 16 and the end piece 22 and enclosed by the elastic sleeve 50 is received with close spacing by a heavy helical spring member 52. The spring has turns of rectangular cross-section to provide for the necessary axial force. A first end of the spring 52 forms an inwardly extending flange 54 on which the end piece 20 rests. The other end forms a flanged seat 56 which has a number of inwardly protruding locking elements 58. The seat 56 receives an annular disc 60 having a circumferential flange 62. The flange 62 has recessed portions 64, so that the disc 60 can be lodged in the seat 56 and locked therein by rotating the disc 60 and flange 62 relative to the locking elements 58 of the seat as shown in FIG. 7.

The disc is provided with three threaded holes 66 which receive set screws 68 by which the pressure bias exerted by the helical spring 52 on the cell stack can be adjusted and equalized.

Figure 8:
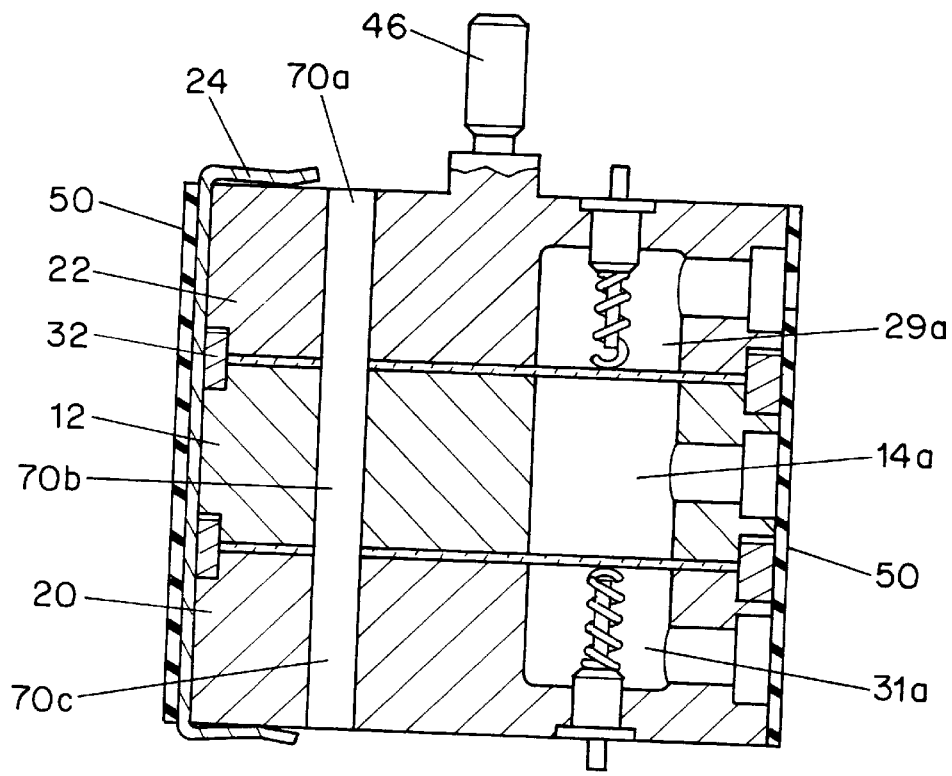
FIG. 8 is a sectional elevation view of still another embodiment of the invention.
Figure 9:
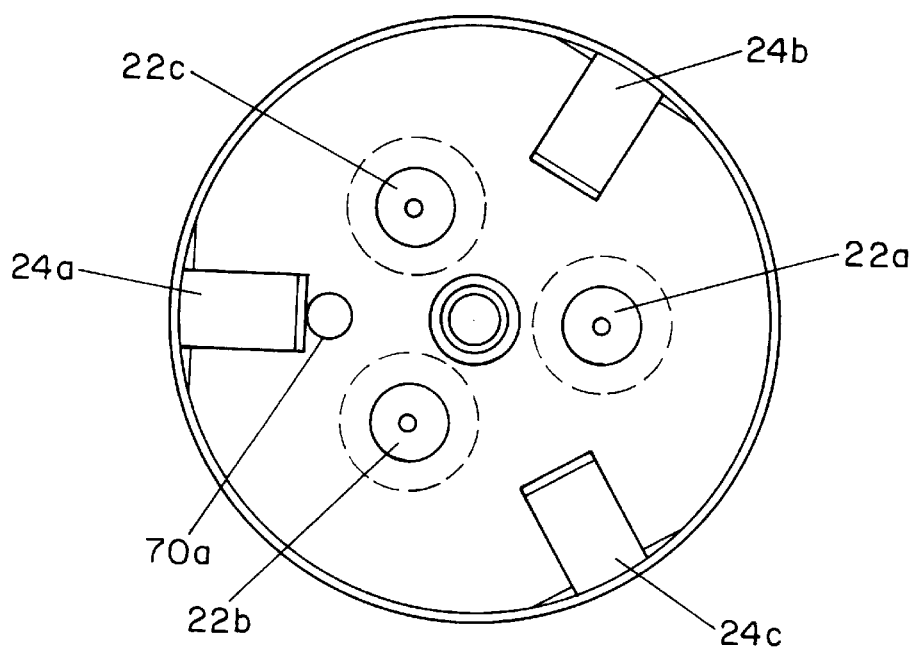
FIG. 9 is a top view of the embodiment of FIG. 8.

The cell shown in FIGS. 8 and 9 corresponds to that of FIGS. 4 and 5 with the exception that it contains a plurality, i.e. three resonator cavities of which one 14a is shown in FIG. 8. The end pieces 20, 22 form corresponding cavities 20a, . . . and 22a, 22b and 22c (FIG. 9). Three clamps 24a, 24b, 24c are used for axially biassing the stack. The end pieces 20, 22 and the main body 12 have mating axial apertures 70a, 70b and 70c, respectively, which receive a thin rod (not shown) for angular alignment of the body 12 and the end pieces 20, 22. The thin elastic sleeve 50 is again shown before the clamping rings 51 are inserted into the radial apertures.

Figure 10:
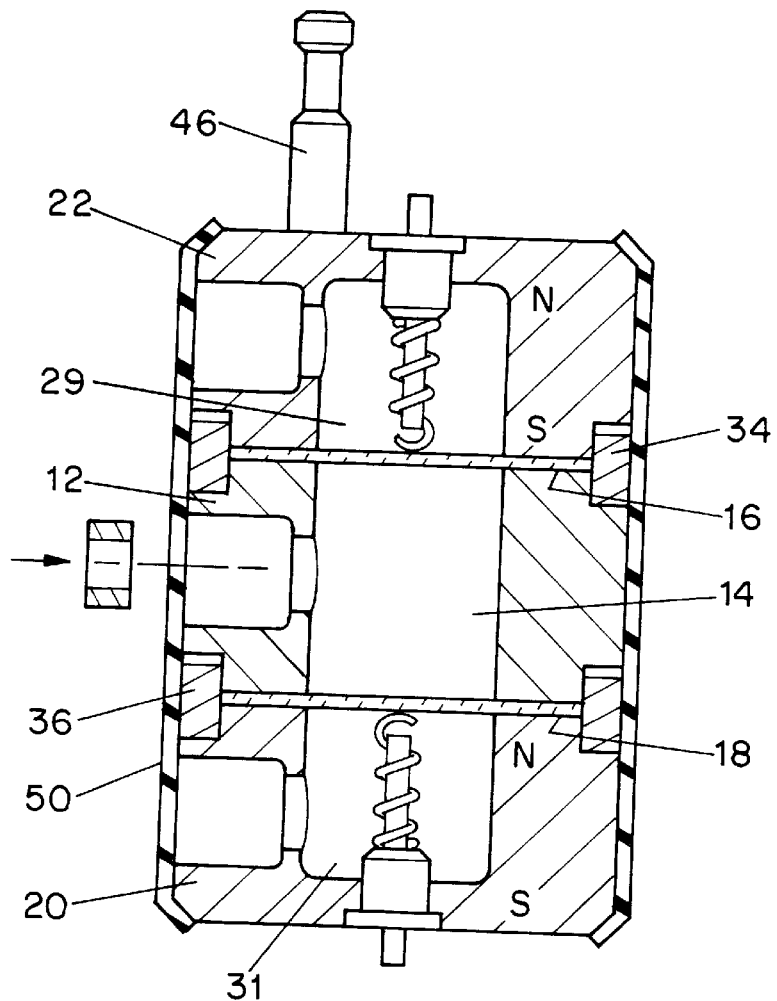
FIG. 10 is an axial section of still another embodiment of the invention along a line A—A of FIG. 11.
Figure 11:
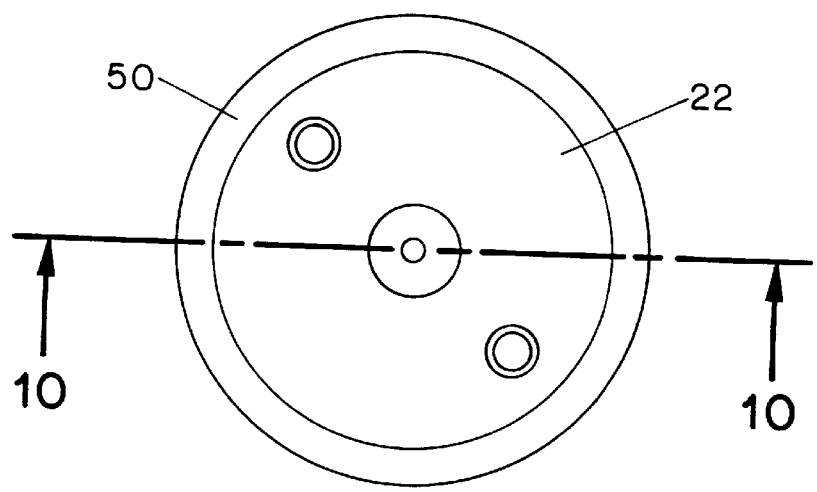
FIG. 11 is a top view of the cell of FIG. 10.

The cell shown in FIGS. 10 and 11 is similar to that of FIGS. 4 and 5 with the exception that the axial force which urges the components of the stack together is generated by the end pieces 20, 22 which are made of permanent magnetic material. The end pieces are magnetized axially as shown in FIG. 10 so that they attract each other and provides the required axial bias. The main body 12 may be made of magnetically soft material, this is, however, not necessary if the magnetic attraction of the opposed opposite poles N–S of the end pieces 20, 22 are strong enough. Filling a magnetic liquid into the ring clearance between the end pieces 20, 22, the main body 12 and the centering rings 34, 36 special additional magnetic and electrical effects may be exerted.

Figure 12:
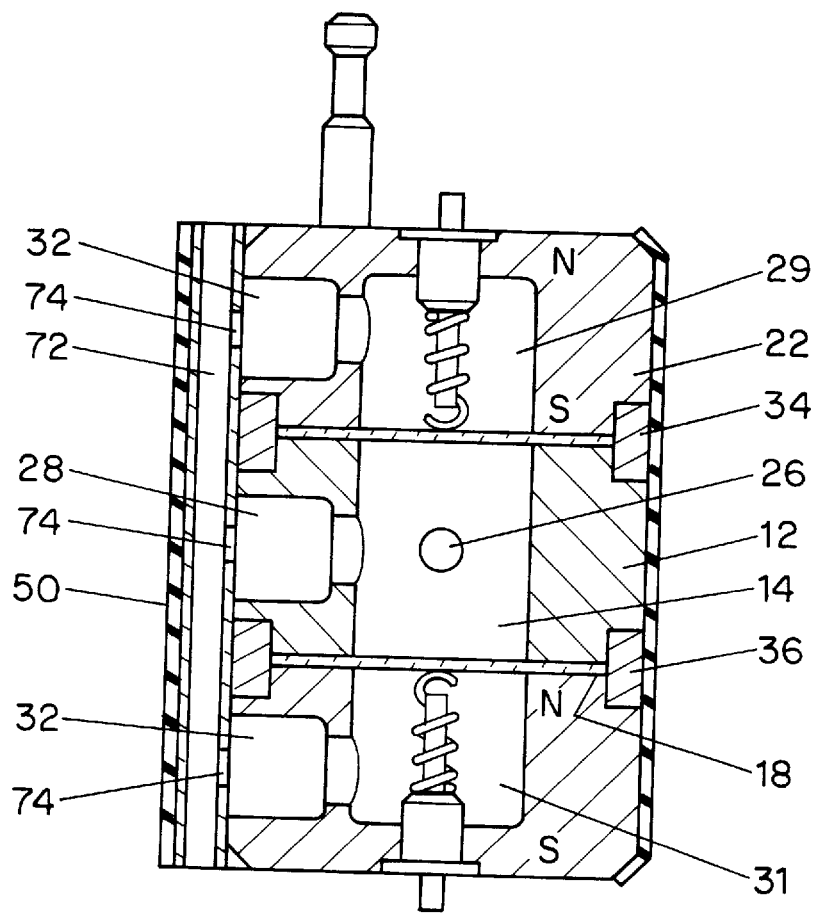
FIG. 12 is an elevation view in section along a line A—A of FIG. 13 of a further embodiment of the invention.
Figure 13:
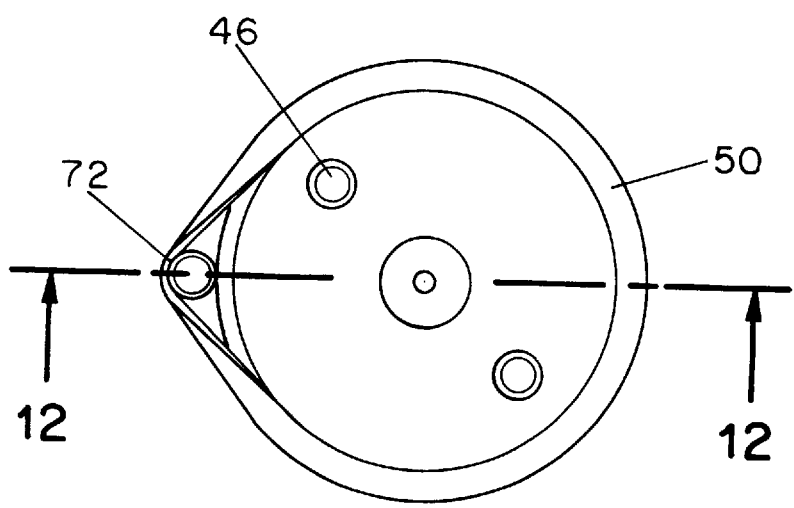
FIG. 13 is a top view of the embodiment of FIG. 12.

The cell shown in FIGS. 12 and 13 is identical with that of FIGS. 10 and 11 with the exception that a drainage and filling tube 72 which may be removable extends axially along the outer walls of the main body 12 and the end pieces 20, 22 adjacent the radial apertures 32, 28. The tube 72 has radial apertures 74 which open into the apertures 28, 32. The tube 72 is kept in place by the elastic sleeve 50 as shown in FIG. 13 and is used for draining gas and supplying liquid during the filling of the cavities 14, 20 and 22, as will be explained in more detail with reference to FIGS. 9a, 19b and 19c. The cell of FIG. 12 may be used also to study liquids under flow conditions. This makes it possible to investigate in cells of the type of FIGS. 10 and 12 the influence of a magnetic field on the fluid properties of magnetic liquids. In this case . . . similar to tube 72. By stopping and restarting the flow at appropriate moments the magnetic relaxation properties of a magnetic liquid may be investigated.

The cell of FIG. 12 may be used for continuous flow measurement of magnetic liquids. In this case the magnetic liquid to be investigated is continuously supplied to cavity 14 via tube 72 and hole 74 communicating with aperture 28 and the liquid is drained via another radial aperture 26 and another axial tube (not shown) similar to tube 72.

Figure 14:
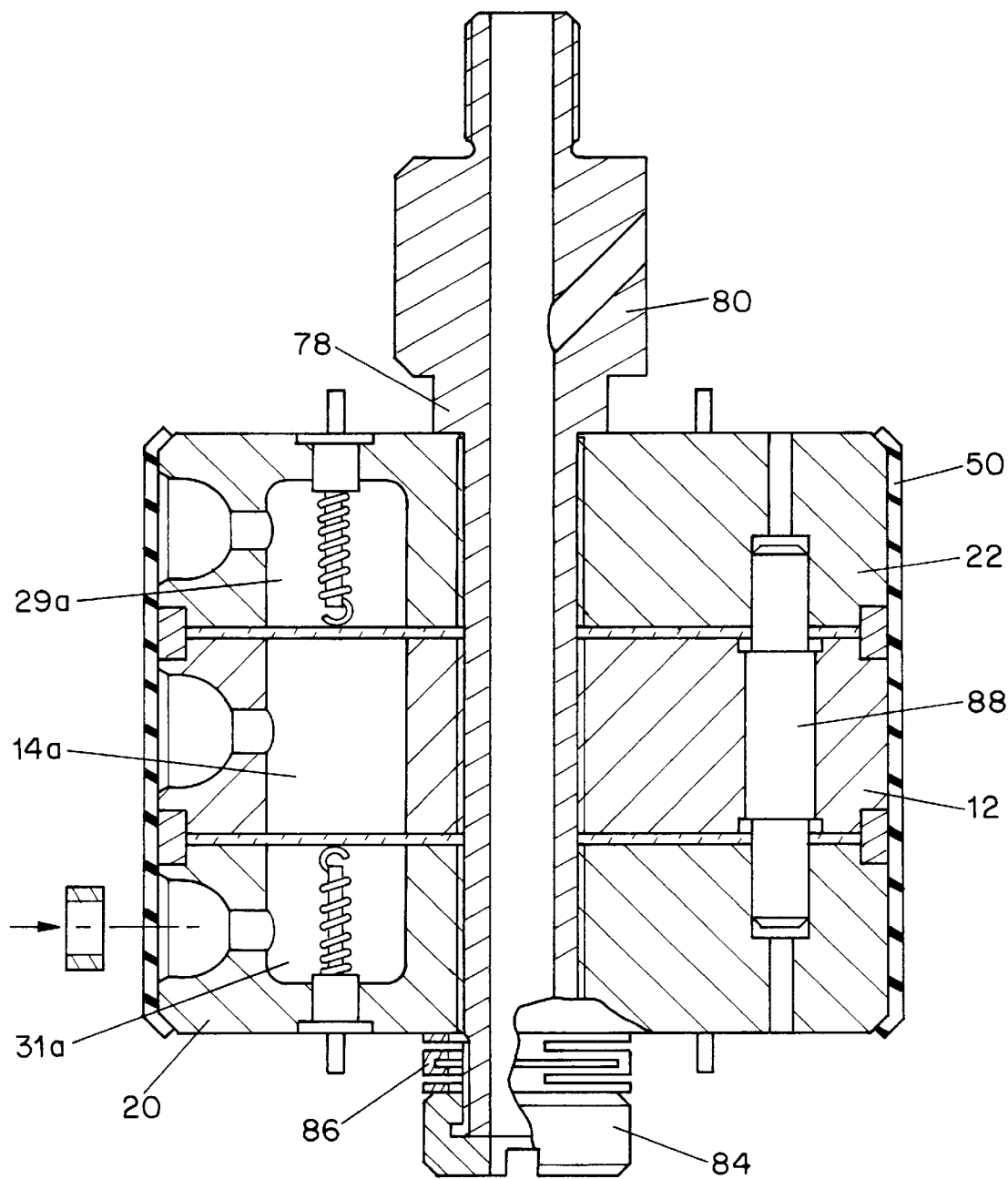
FIG. 14 is an elevation, partially in axial section, of a further embodiment of the invention.
Figure 15:
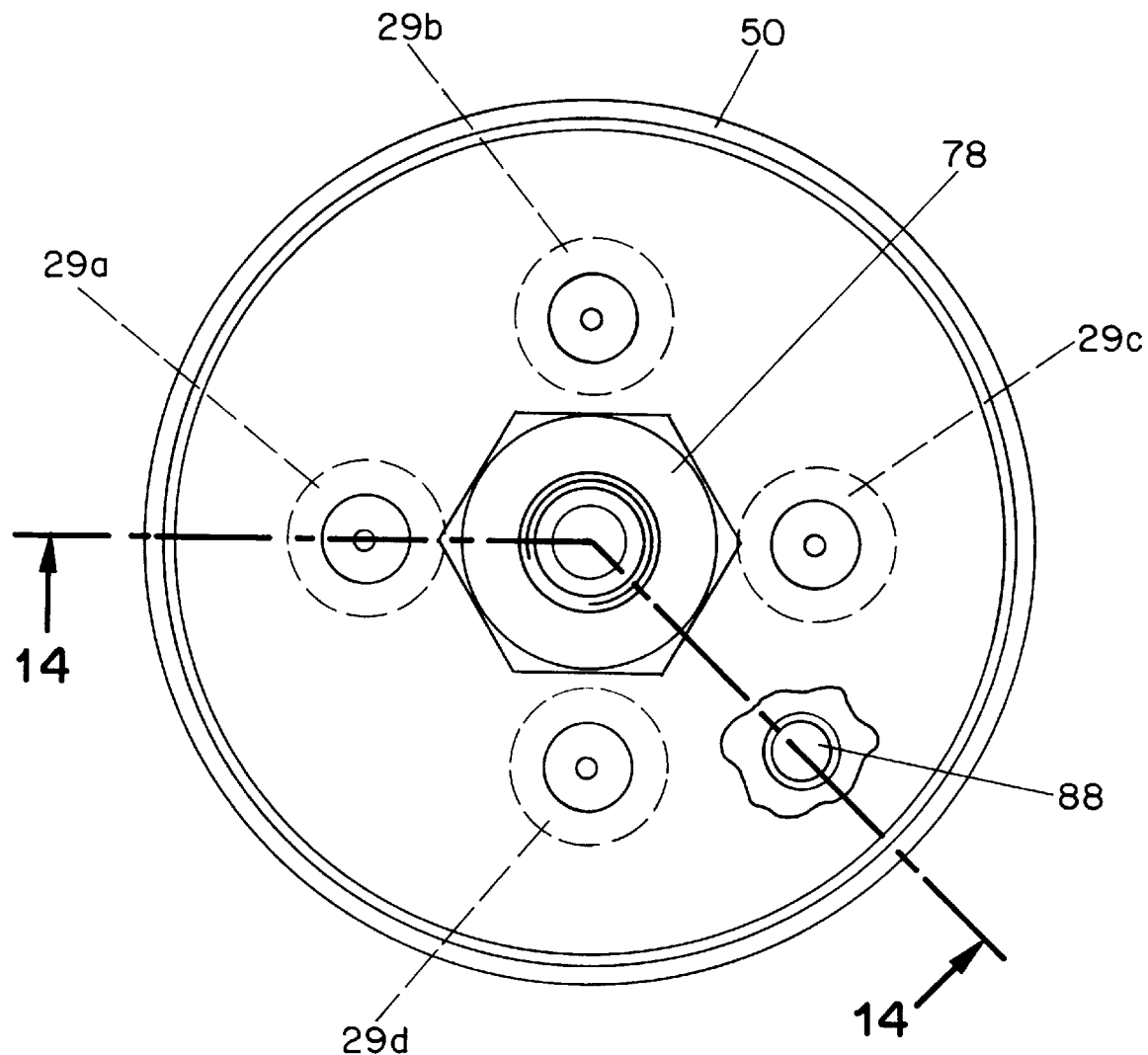
FIG. 15 is a top view of the embodiment of FIG. 14.

The embodiment shown in FIGS. 14 and 15 is a multi-cavity cell similar to that of FIGS. 8 and 9. The main body 12 forms four resonator cavities 14 and a corresponding number of aligned compensation cavities 29a to 29d (FIG. 15). The axial bias is provided by a rod-like central mounting element 78 which extends through aligned central apertures provided in the body 12 and the end pieces 20, 22. At one end, the mounting element 78 has a hexagonal head 80. The other end forms a thread 82 on which a screw cap 84 is mounted. A helical spring 86 or other resilient means is provided between the end piece 20 and the screw cap 84 to provide the required axial bias. The axial bias can be adjusted by the spring constant of the helical spring 86 and the amount of tightening of the screw cap 84. A rod-shaped element 88 seated in mating axial apertures of the body 12 and the end pieces 20, 22 provides for proper angular alignment of body and end pieces.

Figure 16:
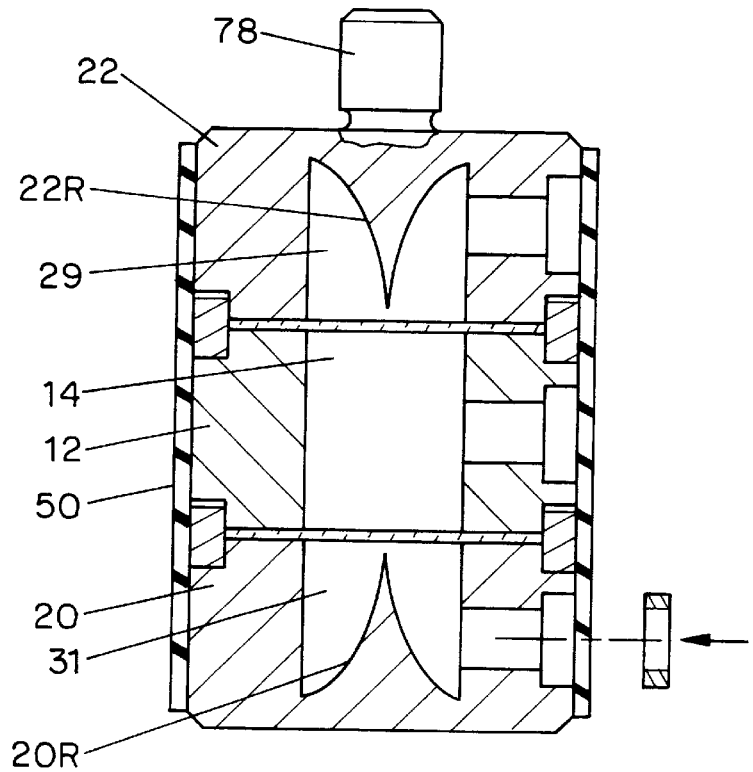
FIGS. 16 and 17 are axial sections of further embodiments.

The cell shown in FIG. 16 has end pieces 20, 22 shaped to reduce reflection of sound waves back to the transducers. More specifically, an inner front wall 20R, 22R of the end pieces 20 and 22, respectively, form a reflector element having essentially the shape of a hyperboloid of revolution or cone to deflect sound waves propagating from the rear side of the respective transducer into the adjacent compensation cavity toward the side wall thereof. Axial holes 90 are provided to accommodate electric terminals (not shown).

Figure 17:
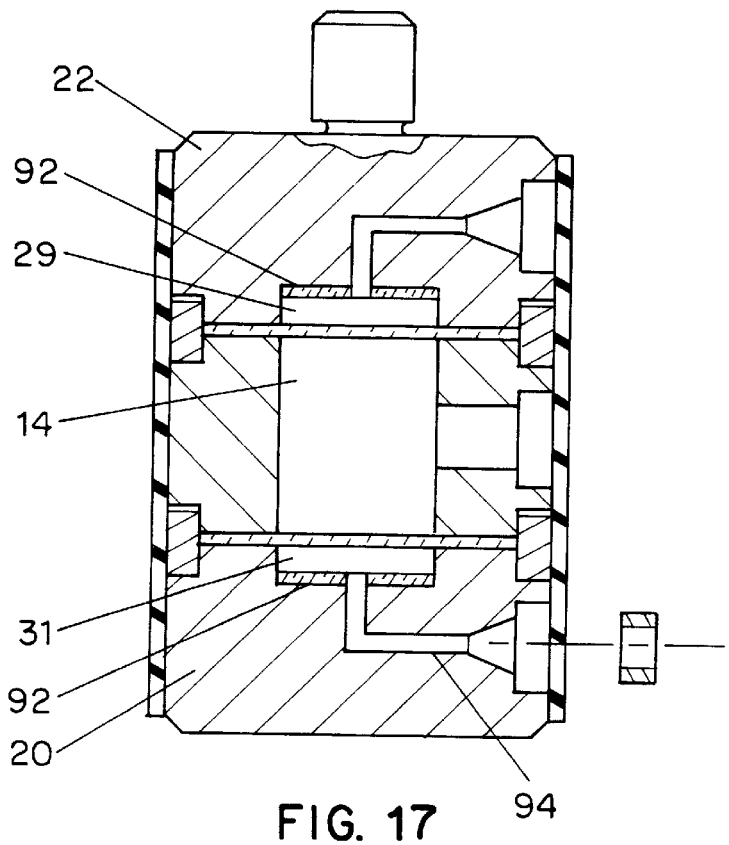

The measurement cell shown in FIG. 17 comprises a layer 92 of sound absorbing material 92 at the bottom of each compensation cavity 29, 31. The sound absorbing material may comprise hollow spherical bodies, preferred diameter 10 to 500 $\mu$m, wall thickness 0.1–10 $\mu$m. At least some of it should have perforated walls. This cell is further modified in that the compensation cavities communicate via channels which have an axial and a radial, countersunk portion as shown in FIG. 17, with the cylindrical outer surface of the respective end piece 20, 22.

Figure 18A:
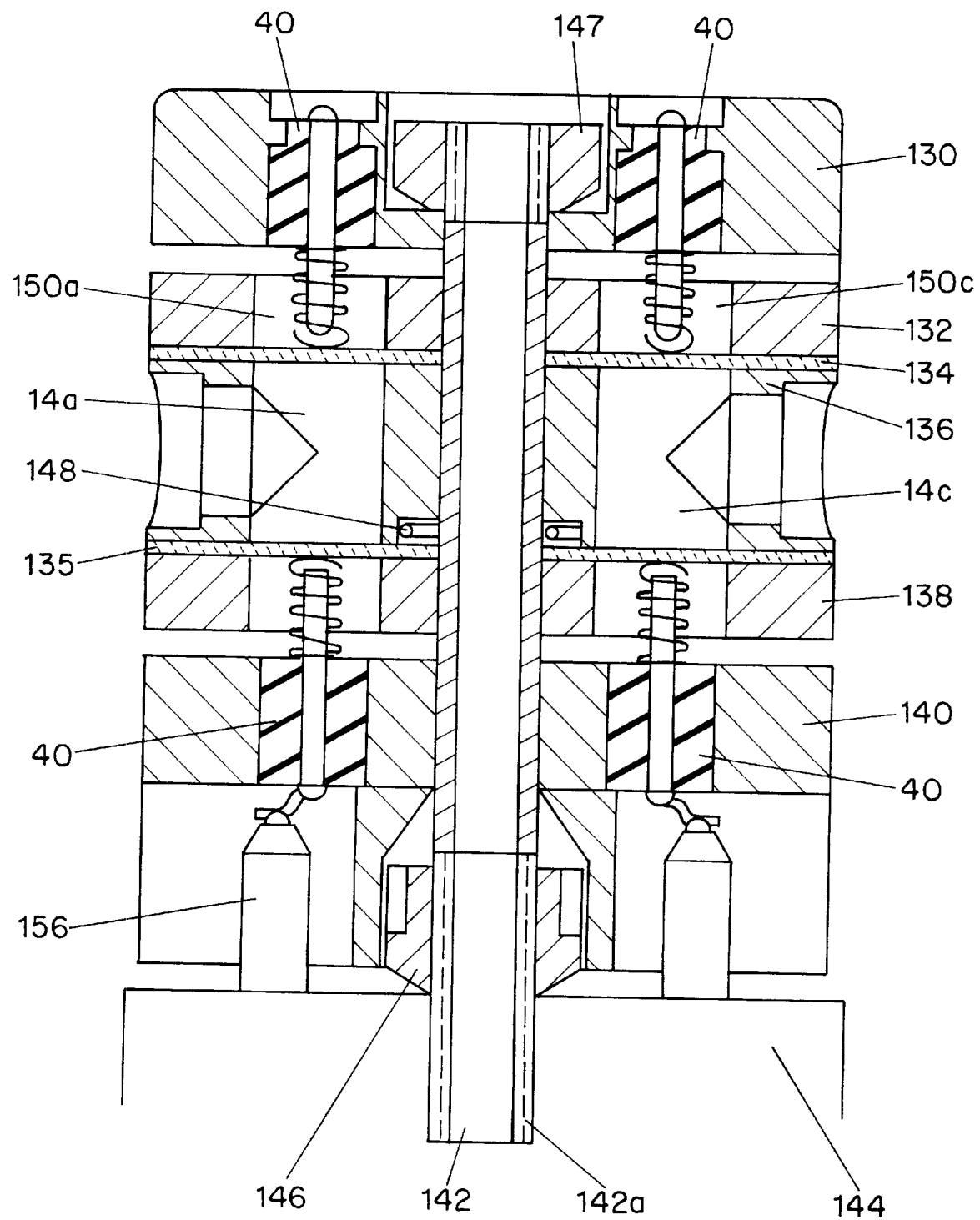
FIG. 18a is an axial section of an at present most preferred embodiment of the invention.

FIG. 18a is a somewhat schematic view, in axial section, of a presently preferred embodiment of the invention. The cell of FIG. 18a comprises, in the order named, an upper contact support disc 130, a first transducer backing disc 132 axially spaced from disc 130, a first electro-acoustical transducer 134, a center piece 136, a second electro-acoustical transducer 135, a second transducer backing disc 138, and a lower contact support disc 140 spaced from disc 138.

All of these elements have a central aperture through which a support tube 142 extends. The support tube 142 has a lower threaded portion 142a which is screwed into a base member 144 and secured by a locking nut 146. A further nut 147 is mounted on an upper thread of the tube 142. Nut 147 has a knive-edge lower end which abuts the bottom of a countersunk portion of the central hole of the upper contact support disc and is adapted to plastic deformation to limit the axial force exerted by the support tube 142—nut 146, 147 system. The components 130, 132, 136, 138, 140 and 142 are made of metal and a spring element 145 seated in an inner circumferential groove of the center piece electrically couples the center piece 36 to the support tube 142 which in turn is grounded through the base member 144.

The center piece 136 forms four resonator cavities of which two cavities 14a, 14b are shown in FIG. 18a.

Figure 18B:
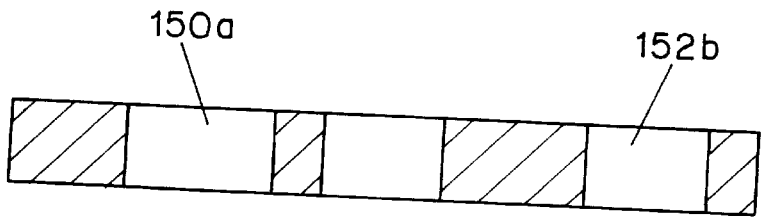
Figure 18C:
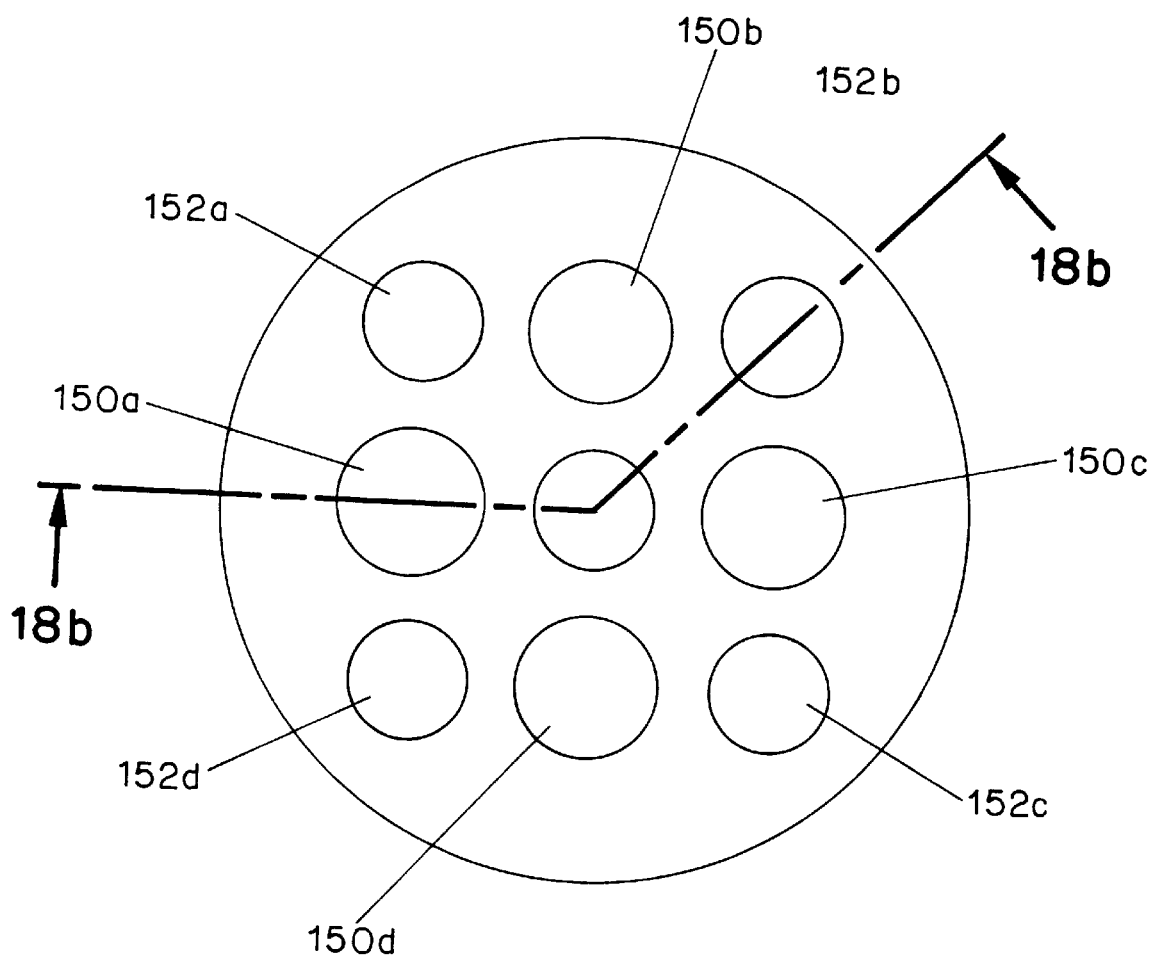

The transducer backing disc 132 shown in axial section in FIG. 18b and in plan view in FIG. 18c has four apertures 150a to 150d which serve as compensation cavities. Four holes 152a to 152d circumferentially offset relative to the apertures 150a to 150d receive bolts (not shown) which extend through corresponding holes in the center piece and the other similar transducer backing disc 138, and are provided with nuts to hold the subassembly consisting of the discs 132, 138, the transducers 134, 135 and the centerpiece 136 together. The spaces between the discs 132, 138 and the discs 130, 140, which form end piece channels, are provided by the bolt heads and the nuts which protrude beyond the abutted surfaces of discs 132, 138.

The upper and lower contact support disks each have four apertures which each receive an insulated terminal structure 40 for supplying high frequency electrical energy to a contacted "hot" electrode of the transducers 134, 135. Each hot electrode is a circular portion of a metal layer on the rear side of the respective transducer wafer insulated by a narrow gap from a surrounding portion of the metal layer abutting the adjacent backing disc. This applies also to the other embodiments described.

The base supports four terminal studs 156 electrically connected to the terminal structures 40 of the lower contact supporting disc 140.

Figure 19A:
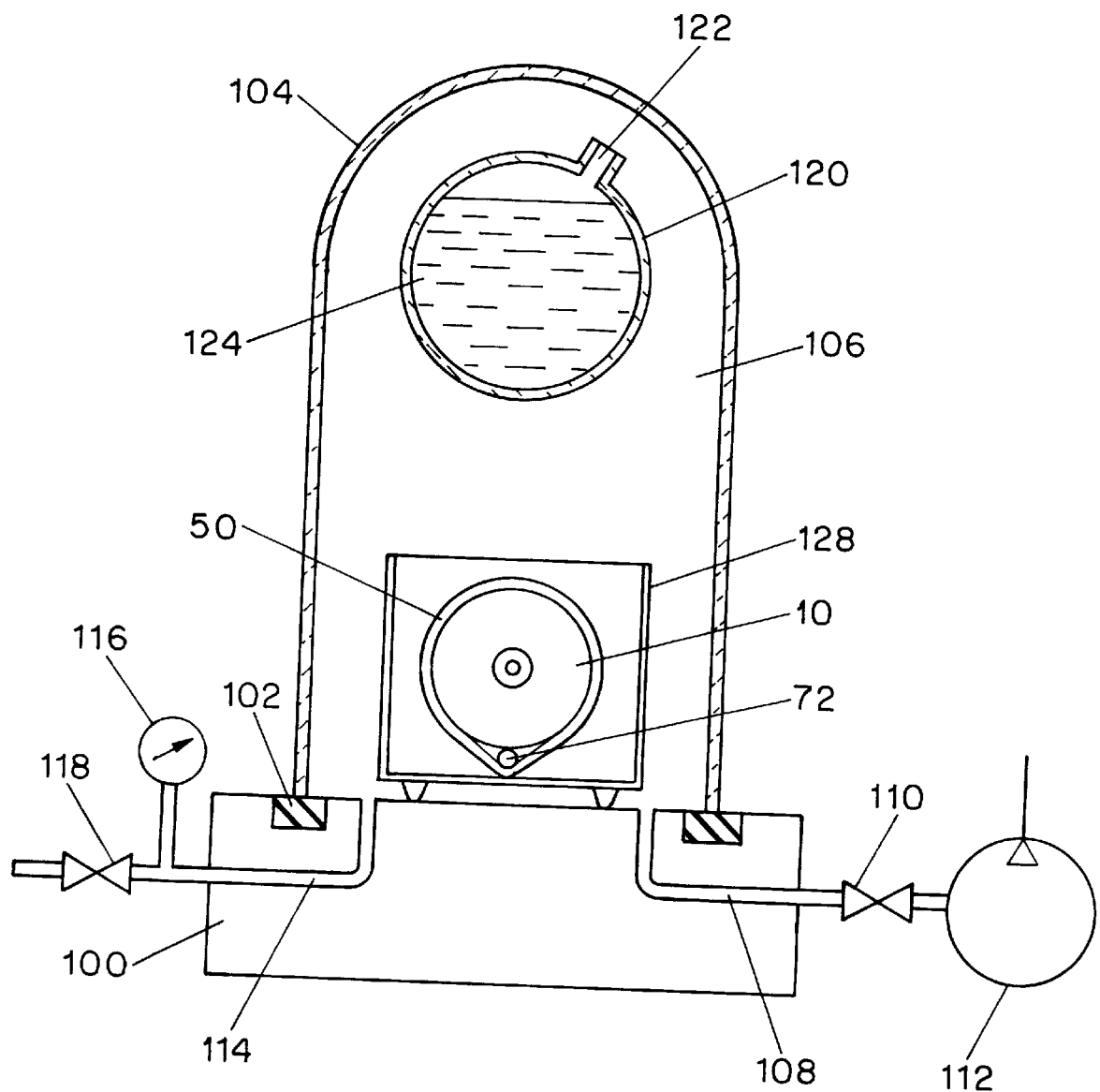
FIG. 19a is a schematic, sectional view of a system for filling a cell of the type shown in FIG. 12.
Figure 19B:
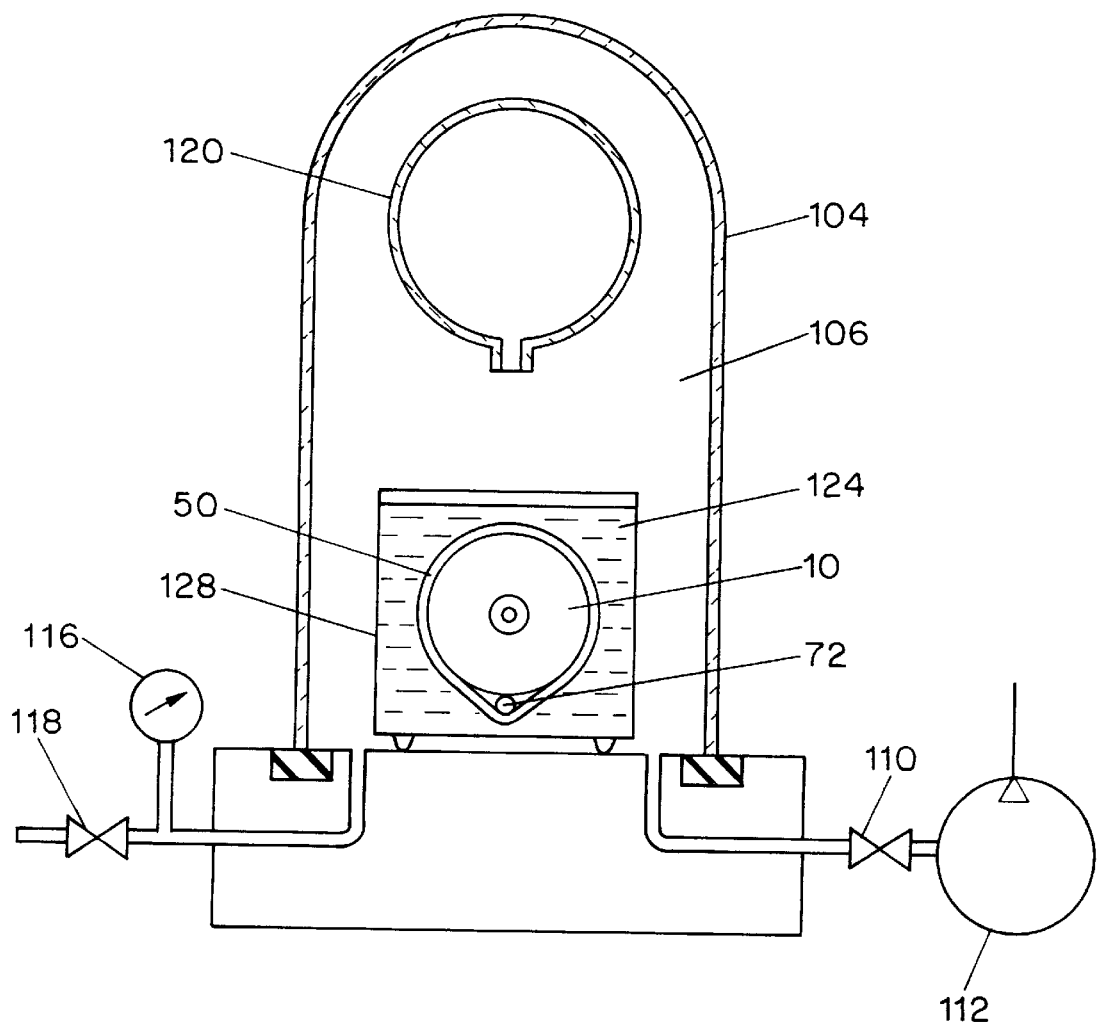
FIGS. 19b and 19c are views of the system of FIG. 19a in subsequent states of operation.
Figure 19C:
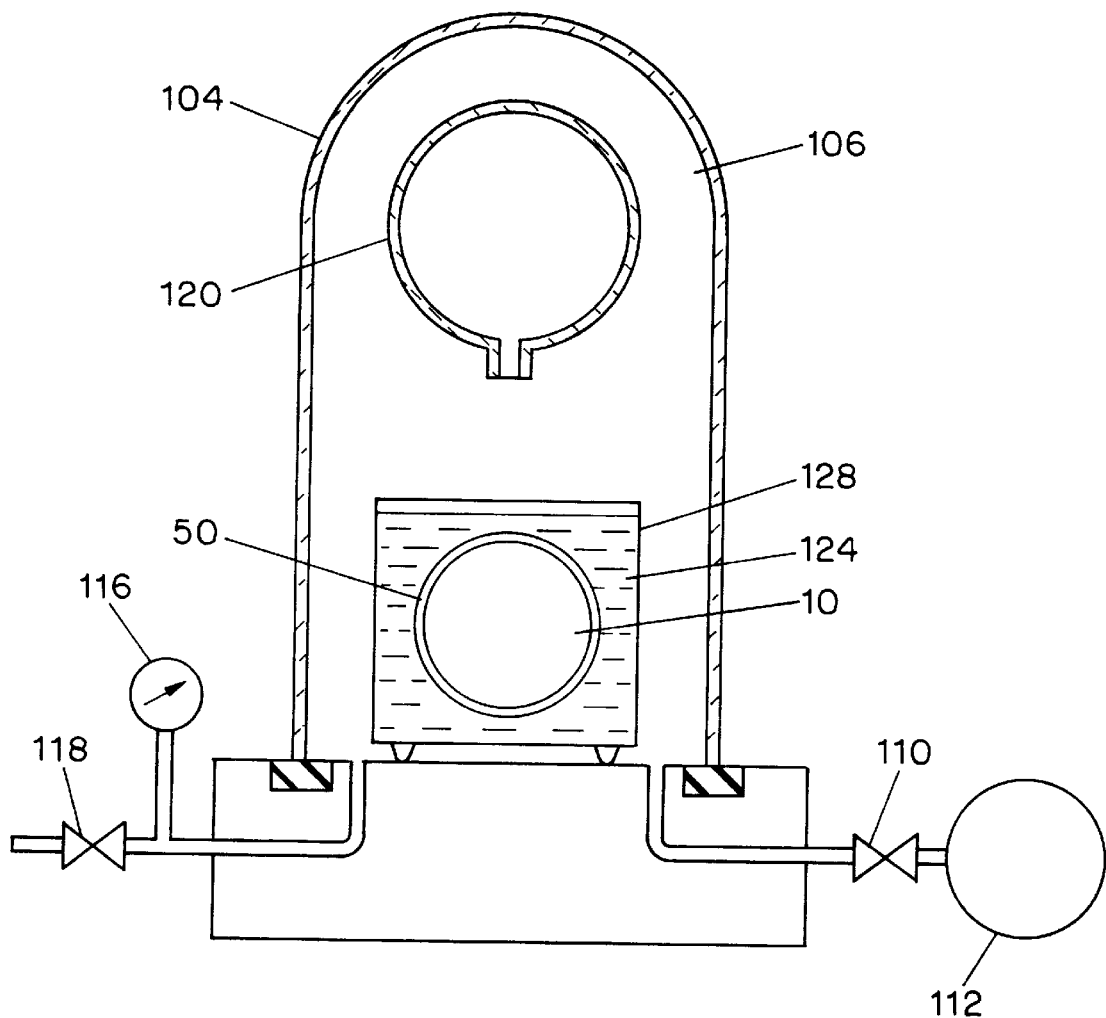

FIGS. 19*a*, 19*b* and 19*c* show an apparatus which can be advantageously used for filling a cell of the types shown in FIGS. 4 to 18 by means of a drainage and filling tube 72 as shown in FIGS. 12 and 13. The apparatus comprises a base 100 having an upper surface with a circular groove in which a seal in form of a rubber O-ring 102 is seated. The apparatus further comprises a dome-shaped cover having an open end which seats on the O-ring 102 to form a closed chamber 106. A first channel 108 which comprises a valve 110 connects the chamber 106 with a vacuum pump 112. A second channel 114 connects the chamber 106 with a pressure gauge 116 and via a valve 118 with the atmosphere.

A container 120 having an outlet 122 and being adapted to contain a liquid sample 124 to be investigated or another liquid to be introduced into the sample or compensation cavities is mounted rotably in an upper portion of the chamber 106. The sample container 120 is coupled to a remotely controllable device (not shown) which enables the container to rotate from the position shown in FIG. 19*a* to the position shown in FIG. 19*b*.

A trough 128 adapted to receive a cell 10 to be filled is provided in the lower portion of the chamber 106 below the container (120).

In operation, the container 120 is filled with a liquid 124 to be introduced into the sample cavity and/or the compensation cavities of a sample cell 10. The sample cell 10 to be filled is provided with a drainage and filling tube 72 as shown in FIGS. 12 and 13 and placed into the trough 128. Then the cover 104 is seated on the O-ring 102 to seal the chamber 106.

Air and vapors are evacuated from the chamber by the pump 112 until the pressure in the chamber 106 is slightly higher than the vapor pressure of the liquid 124. This removes the air from the chamber 106 and degasses the liquid 124 without altering the composition of the liquid by selective evaporation. During this step, valve 118 is closed and valve 110 is open.

When the air is removed from the chamber 106 and the fluid in the container 120 is degassed, valve 110 is closed. The container 120 is rotated into the position shown in FIG. 19*b* to transfer the liquid 124 from the container 120 into the trough 128. The volume of the liquid should be sufficient to completely cover the cell 10 in the trough 128. Then, valve 118 is opened to admit air into the chamber 106 which causes the liquid 124 to enter the cavities 28, 32 (FIG. 12) through the tube 72 and the radial apertures 74. If all three cavities are filled simultaneously, the fluid 124 used is sample fluid or a gauge fluid.

In the next step, the tube 72 is removed while the cell 10 is maintained submerged. When the tube 72 is removed, the elastic sleeve 50 automatically closes the radial apertures. The final sealing is then effected by urging clamping rings 51 into the countersunk portions of the apertures 28, 32. The thin elastic sleeve is pressed by the rings into the countersunk portions and seals the force seat so that it can withstand pressure differences.

Figure 20:
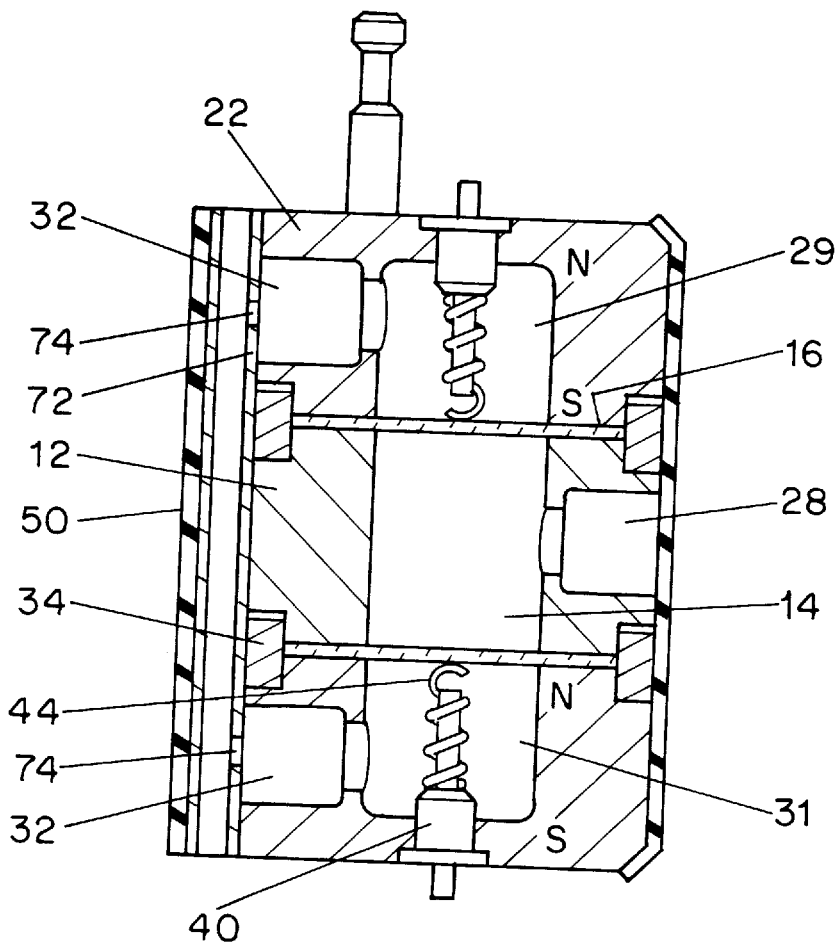
FIG. 20 is an elevation view in axial section of a still further embodiment of the invention.
Figure 21:
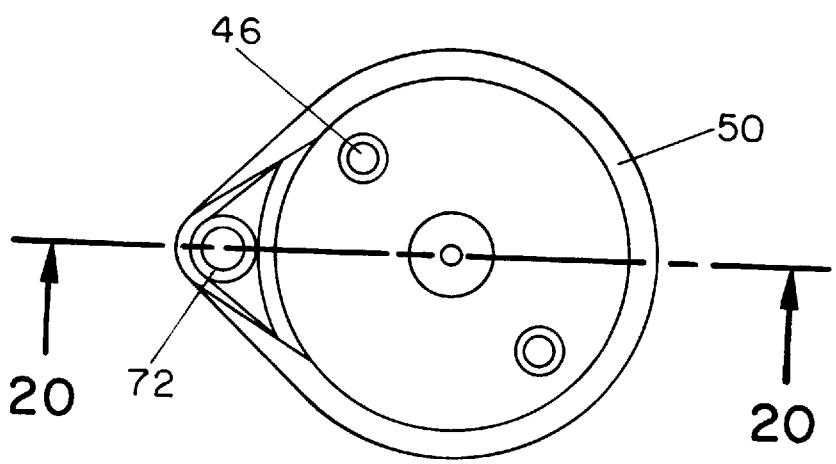
FIG. 21 is a top view of the embodiment of FIG. 20.

FIGS. 20 and 21 show a cell, which allows the filling of the sample cavity 14 on the one hand and the compensation cavities 29, 31 on the other hand with different liquids. The cell of FIGS. 20 and 21 is similar to that of FIGS. 12 and 13 with the exception that the radial aperture 28 is on the opposite side as the radial apertures 32, 34.

First, the compensation cavities 29, 31 are filled, as described with reference to FIGS. 19*a* to 19*c* using a tube 72 having a pair of radial apertures 74, and thereafter, the sample cavity 14 is filled with a tube 72 (not shown) having one radial aperture aligned with the aperture 28.

If the compensation cavities 29, 31 are filled with a liquid, e.g. the liquid used for pressurizing the cell, which differs from the sample fluid with which the sample cavity 14 is filled, preferably, the following condition as mentioned already above is met:

$$2(C/C_0)+C\beta_0 V_0 = C_1 \beta_1 V_1$$

We claim:

1. A cell for measuring the acoustical properties of a fluid sample, said cell comprising:
   a main cell having
      (a) a cell body having first and second flat cell ends opposite each other,
      (b) first and second cell openings in said first and second flat cell ends, respectively,
      (c) a fluid sample cavity in said cell body for receiving the fluid sample, said fluid sample cavity being in communication with said first and second cell openings, and
      (d) a fluid sample channel connecting said fluid sample cavity and the outer surface of said cell body;
   first and second electro-acoustical transducer wafers disposed on said first and second flat cell ends, respectively, each of said first and second electro-acoustical transducer wafers having an inner surface facing inwardly toward said fluid sample cavity and an outer surface facing outwardly away from said fluid sample cavity;
   first and second inner electrodes disposed on the inner surfaces of said first and second electro-acoustical transducer wafers, respectively;
   first and second outer electrodes disposed on the outer surfaces of said first and second electro-acoustical transducer wafers, respectively;
   a first end piece having
      (a) a first end-piece body with two ends,
      (b) a first end-piece end-wall at one end of said end-piece body,
      (c) a first flat end-piece face at the other end of said end-piece body, said first flat end-piece face being placed in contact with the outer surface of said first electro-acoustical transducer wafer,
      (d) a first end-piece opening in said first flat end-piece face, said first end-piece opening being approximately the size of and being aligned with said first cell opening,
      (e) a first compensation fluid cavity for receiving a compensation fluid, said first compensation fluid cavity being in communication with said first end-piece opening, and
      (f) a first compensation fluid channel connecting said first compensation fluid cavity and the outer surface of said first end-piece body;
   a second end piece having
      (a) a second end-piece body with two ends,
      (b) a second end-piece end-wall at one end of said end-piece body,
      (c) a second flat end-piece face at the other end of said end-piece body, said second flat end-piece face being placed in contact with the outer surface of said second electro-acoustical transducer wafer, (d) a second end-piece opening in said second flat end-piece face, said second end-piece opening being approximately the size of and being aligned with said second cell opening, (e) a second compensation fluid cavity for receiving a compensation fluid, said second compensation fluid cavity being in communication with said second end-piece opening, and (f) a second compensation fluid channel connecting said second compensation fluid cavity and the outer surface of said second end-piece body;

first and second terminals mounted in said first and second end pieces, respectively, said first and second terminals electrically coupled to said first and second outer electrodes, respectively;

means for applying pressure to said first and second end pieces to bias them towards each other; and one or more elastic sleeves tightly enclosing said cell body and said first and second end-piece bodies.

2. The cell of claim 1, further comprising an annular member positioned over said one or more elastic sleeves and fitted into said fluid sample channel, whereby said annular member forces a portion of said one or more elastic sleeves into the fluid sample channel, thereby forming a pressure resistant seal between said fluid sample channel and said one or more elastic sleeves.

3. The cell of claim 1, further comprising first and second annular members positioned over said one or more elastic sleeves and fitted into said first and second compensation fluid channels, respectively, whereby said first and second annular members force first and second portions of said one or more elastic sleeves into said first and second compensation fluid channels, respectively, thereby forming pressure resistant seals between said first and second compensation fluid channels and said one or more elastic sleeves.

4. The cell of claim 1, wherein said first and second end-piece end-walls comprise first and second apertures, respectively, in which said first and second terminals are mounted, respectively, in a pressure-resistant, sealing manner.

5. The cell of claim 1, wherein said first and second flat cell ends have a polished finish.

6. The cell of claim 14, wherein said means for applying pressure comprises at least one essentially C-shaped clamp.

7. The cell of claim 1, wherein said means for applying pressure comprises at least one helical spring surrounding said cell body.

8. The cell of claim 1, wherein said means for applying pressure comprises a spring-loaded rod centrally disposed through said cell body and said first and second end pieces.

9. The cell of claim 1, further comprising a second fluid sample channel formed between said fluid sample cavity and the outer surface of said cell body, and an elastic plug urged into said second fluid sample channel.

10. The cell of claim 1, wherein the outer surfaces of said cell body and said first and second end-piece bodies comprise annular grooves surrounding said first and second electro-acoustical transducer wafers.

11. The cell of claim 10, further comprising annular members mounted in said first and second annular grooves, respectively.

12. The cell of claim 1, wherein said first and second end-piece end-walls have first and second projections extending into said first and second compensation fluid cavities, respectively, said first and second projections having essentially conical surfaces.

13. The cell of claim 1, wherein the opening of said fluid sample channel on the outer surface of said cell body is angularly displaced with respect to the opening of said first and second compensation fluid channels on the outer surfaces of said first and second end-piece bodies, respectively.

14. The cell of claim 1, wherein the interior surfaces of the first and second end pieces comprise a sound absorbing material thereon.

15. The cell of claim 1, wherein said one or more elastic sleeves comprise a body sleeve tightly enclosing said cell body and first and second end-piece sleeves tightly enclosing said first and second end-piece bodies, and wherein the following condition is met:

$$2(C/C_0)+C\beta_0 V_0 = C_1 \beta_1 V_1,$$

wherein $C$ is the volume elasticity of said body sleeve;

$C_0$ is the volume elasticity of said first and second electro-acoustical transducer wafers;

$C_1$ is the volume elasticity of each of said first and second end-piece sleeves;

$\beta_0$ is the coefficient of compressibility of the sample fluid;

$\beta_1$ is the coefficient of compressibility of the compensation fluid;

$V_0$ is the volume of said sample fluid cavity; and $V_1$ is the volume of each of said first and second compensation fluid cavities.

16. The cell of claim 1, wherein said cell body, said first end-piece body, and said second end-piece body are cylinders sharing a common cylindrical axis, and wherein said fluid sample channel, said first compensation fluid channel, and said second compensation fluid channel are aligned with radial axes of said cylinders.

* * * * *

UNITED STATES PATENT AND TRADEMARK OFFICE
CERTIFICATE OF CORRECTION

PATENT NO. : 5,836,200

DATED : November 17, 1998

INVENTOR(S) : Belonenko et al.

It is certified that error appears in the above-identified patent and that said Letters Patent is hereby corrected as shown below:

Title page, item [56] References Cited, U.S. PATENT DOCUMENTS: "2,521,634 3/1950 Janssen et al." should read -- 2,521,634 9/1950 Janssen et al. --.

Signed and Sealed this

Fourteenth Day of March, 2000

Attest:

Attesting Officer

Q. TODD DICKINSON

Commissioner of Patents and Trademarks